US009072794B2

(12) United States Patent
Woo et al.

(10) Patent No.: US 9,072,794 B2
(45) Date of Patent: Jul. 7, 2015

(54) LONG-ACTING GLUCAGON CONJUGATE AND PHARMACEUTICAL COMPOSITION COMPRISING THE SAME FOR THE PREVENTION AND TREATMENT OF OBESITY

(75) Inventors: Young Eun Woo, Daejeon (KR); Jong Soo Lee, Seongnam-si (KR); Ling Ai Shen, Seoul (KR); Dae Jin Kim, Hwaseong-si (KR); Sung Youb Jung, Suwon-si (KR); In Young Choi, Yongin-si (KR); Se Chang Kwon, Seoul (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 69 days.

(21) Appl. No.: 13/810,999

(22) PCT Filed: Jul. 21, 2011

(86) PCT No.: PCT/KR2011/005375
§ 371 (c)(1),
(2), (4) Date: Jan. 18, 2013

(87) PCT Pub. No.: WO2012/011752
PCT Pub. Date: Jan. 26, 2012

(65) Prior Publication Data
US 2013/0122023 A1 May 16, 2013

(30) Foreign Application Priority Data

Jul. 21, 2010 (KR) .................... 10-2010-0070484
Jul. 21, 2010 (KR) .................... 10-2010-0070485

(51) Int. Cl.
*A61K 39/385* (2006.01)
*A61K 39/00* (2006.01)
*A61K 38/26* (2006.01)
*A61K 38/00* (2006.01)
*A61K 38/22* (2006.01)
*A61K 47/48* (2006.01)
*A61K 31/4164* (2006.01)
*A61K 45/06* (2006.01)
*C07K 14/605* (2006.01)

(52) U.S. Cl.
CPC ....... *A61K 47/48415* (2013.01); *A61K 31/4164* (2013.01); *A61K 38/26* (2013.01); *A61K 45/06* (2013.01); *A61K 47/48369* (2013.01); *C07K 14/605* (2013.01); *A61K 47/48692* (2013.01)

(58) Field of Classification Search
None
See application file for complete search history.

(56) References Cited

U.S. PATENT DOCUMENTS

| 5,480,867 A * | 1/1996 | Merrifield et al. ........... 514/11.7 |
| 5,665,705 A | 9/1997 | Merrifield et al. |
| 6,277,375 B1 | 8/2001 | Ward |
| 7,157,555 B1 * | 1/2007 | Beeley et al. .................. 530/324 |
| 8,450,270 B2 * | 5/2013 | Dimarchi et al. .............. 514/6.8 |
| 2006/0269553 A1 * | 11/2006 | Kim et al. .................. 424/155.1 |
| 2009/0181912 A1 * | 7/2009 | Wang et al. ..................... 514/44 |

FOREIGN PATENT DOCUMENTS

| KR | 10-2005-0047032 A | 5/2005 |
| KR | 10-2006-0106486 A | 10/2006 |
| KR | 10-0725315 B1 | 6/2007 |
| KR | 10-2008-0064750 A | 7/2008 |
| WO | 2006107124 A1 | 10/2006 |
| WO | 2008082274 A1 | 7/2008 |
| WO | 2008/152403 A1 | 12/2008 |
| WO | 2009/058662 A2 | 5/2009 |
| WO | 2009/069983 A2 | 6/2009 |

OTHER PUBLICATIONS

Melnikova et al 2006. Nature Rev. Drug Dis. 5:369-370.*
Kendall et al. 2005. Diabetes Care 28:1083-1091.*
Heppner et al. 2010. Physiology and Behavior. 100:545-548.*
International Searching Authority International Search Report for PCT/KR2011/005375 dated Apr. 4, 2012.
Robberecht et al., "Comparative Efficacy of Seven Synthetic Glucagon Analogs, Modified in Position 1, 2 and/or 12, on Liver and Heart Adenylate Cyclase From Rat," Peptides, 1986, vol. 7, pp. 109-112.
Day et al., "A New Glucagon and GLP-1 Co-Agonist Eliminates Obesity in Rodents," Nature Chemical Biology, 2009, vol. 5, No. 10, pp. 749-757.
Korean Patent Office, Korean Office Action issued in corresponding KR Application No. 10-2011-0070535, dated Apr. 19, 2013.
European Patent Office, Communication dated Jun. 2, 2014, issued in corresponding European Application No. 11809879.
Stigsnaes et al., "Characterisation and physical stability of PEGylated glucagon", International Journal of Pharmaceutics, Elsevier B.V., 2007, vol. 330, Issue 1-2, pp. 89-98.
Taiwan Intellectual Property Office, Communication dated Jun. 27, 2014, issued in corresponding Taiwanese Application No. 100125894.
Taiwan Intellectual Property Office, Communication dated Jan. 21, 2014, issued in corresponding Taiwanese Application No. 10320086280.

* cited by examiner

*Primary Examiner* — Shulamith H Shafer
(74) *Attorney, Agent, or Firm* — Sughrue Mion, PLLC

(57) ABSTRACT

Disclosed is a novel long-acting glucagon conjugate in which glucagon or its derivative is covalently linked to a polymer carrier via a non-peptide linker, and a pharmaceutical composition comprising the same as an effective ingredient useful for the prevention and treatment of obesity. Since the long-acting glucagon conjugate of the present invention shows improved in vivo durability and stability, when used in combination with an anti-obesity drug, it is possible to induce synergistic effects on the loss of body weight and decrease in food intake without causing any side-effects such as fluctuation in blood glucose level. Accordingly, the long-acting peptide conjugate of the present invention is very effective for the prevention and treatment of obesity.

42 Claims, 5 Drawing Sheets

```
SEQUENCE LISTING

<160> NUMBER OF SEQ ID NOS: 3

<210> SEQ ID NO 1
<211> LENGTH: 29
<212> TYPE: PRT
<213> ORGANISM: Camelus dromedarius
<220> FEATURE:
<221> NAME/KEY: CDS
<222> LOCATION: 1..29
<223> OTHER INFORMATION: glucagon

<400> SEQUENCE: 1

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr
            20                  25

<210> SEQ ID NO 2
<211> LENGTH: 39
<212> TYPE: PRT
<213> ORGANISM: Heloderma suspectum
<220> FEATURE:
<221> NAME/KEY: CDS
<222> LOCATION: 1..39
<223> OTHER INFORMATION: exendin-4

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 3
<211> LENGTH: 28
<212> TYPE: PRT
<213> ORGANISM: Artificial
<220> FEATURE:
<223> OTHER INFORMATION: Synthetic construct

<400> SEQUENCE: 3

Ser Gln Gly Thr Phe Thr Ser Asp Tyr Ser Lys Tyr Leu Asp Ser Arg
 1               5                  10                  15

Arg Ala Gln Asp Phe Val Gln Trp Leu Met Asn Thr
                20                  25
```

LONG-ACTING GLUCAGON CONJUGATE AND PHARMACEUTICAL COMPOSITION COMPRISING THE SAME FOR THE PREVENTION AND TREATMENT OF OBESITY

CROSS REFERENCE TO RELATED APPLICATIONS

This application is a National Stage of International Application No. PCT/KR2011/005375 filed Jul. 21, 2011, claiming priority based on Korean Patent Application Nos. 10-2010-0070484 filed Jul. 21, 2010 and 10-2010-0070485 filed Jul. 21, 2010, the contents of all of which are incorporated herein by reference in their entirety.

TECHNICAL FIELD

The present invention relates to a novel long-acting glucagon conjugate and a pharmaceutical composition comprising the same for the prevention and treatment of obesity. More particularly, the present invention relates to a novel long-acting glucagon conjugate in which glucagon or its derivative is covalently linked to a polymer carrier via a non-peptide linker, and a pharmaceutical composition comprising the same as an effective ingredient for the prevention and treatment of obesity. Since the long-acting glucagon conjugate of the present invention shows improved in vivo durability and stability, when used in combination with an anti-obesity drug, it is possible to significantly reduce the dose of the drugs co-administered and exhibit better drug compliance without fluctuation in blood glucose level. Accordingly, the long-acting glucagon conjugate of the present invention can be effectively used for preventing and treating obesity.

BACKGROUND ART

The recent economic advances and lifestyle changes have been accompanied by great changes in dietary habit. Particularly, busy people of today are overweight and obese due to high-calorie diets and insufficient exercise. The World Health Organization (WHO) has reported that more than one billion adults are overweight worldwide, among them over three million are clinically diagnosed with severe obesity, and 25,000 people die of overweight- or obesity-related diseases every year (World Health Organization, Global Strategy on Diet, Physical Activity and Health, 2004).

Overweight and obesity increase blood pressure and blood cholesterol level, thereby increasing the risk of various adult diseases including heart disease, diabetes, arthritis, etc. Further, overweight and obesity are one of the main causes for inducing adult diseases such as arteriosclerosis, hypertension, hyperlipidemia and heart disease in children and adolescents.

Obesity is now recognized as a serious disease prevalent over the world and is a cause of various diseases. However, it is not readily curable. Medical specialists have the conception that obesity is not merely a problem of self-control but is a complicated disease which is closely related to appetite control and energy metabolism. Obesity results from excessive energy intake relative to energy consumption. At the individual level, a combination of excessive food energy intake and a lack of physical activity is thought to explain most cases of obesity. Therefore, in the long-term, there is an urgent need to develop a medicine which is effective and safe in the prevention and treatment of obesity when used in combination with diet therapy and physical activity.

In recent medicinal research on obesity, keen attention has been paid to oxyntomodulin, which is derived from pre-glucagon and can bind to both the GLP-1 and glucagon receptors. The development of an anti-obesity drug based on such a dual function of oxyntomodulin has been actively studied.

Glucagon-like peptide-1 (hereinafter, referred to as 'GLP-1') is a drug under development for hyperglycemia in diabetic patients and possesses several physiological functions of increasing insulin synthesis and secretion, decreasing glucagon secretion, inhibiting gastric emptying, enhancing the use of glucose and decreasing food intake. Also, exendin-4 which is secreted by lizard venom and shows about 50% homology with GLP-1, is known to alleviate hyperglycemia in diabetes patients by activating the GLP-1 receptor.

Glucagon is secreted by the pancreas when blood glucose levels fall too low due to, for example, drug treatment, disease, hormones or enzyme deficiency. Glucagon signals the liver to break down glycogen to glucose and release more glucose into the blood stream, which results in raising blood glucose level.

Acting as an agonist to both the GLP-1 receptor and the glucagon receptor, oxyntomodulin has the functions of decreasing food intake like GLP-1 and digesting glycogen like glucagon, and thus is a potential anti-obesity agent.

As an oxyntomodulin derivative, there are a dual agonist peptide (Merck) in phase 1 clinical trials, and ZP2929 (Zealand, WO 2008/152403A1) in pre-clinical trials. The dual agonist peptide (Merck) is an oxyntomudulin derivative whose resistance to dipeptidyl peptidase-IV (hereinafter, referred to as 'DPP-IV') is increased by substituting the 2nd amino acid L-Ser with D-Ser, and blood half-life is prolonged by conjugating a cholesterol moiety to the C-terminal end thereof. ZP2929 (Zealand) is an oxyntomodulin derivative which includes substitutions of the 2nd amino acid L-Ser with D-Ser to increase resistance to DPP-IV, the 17th amino acid Arg with Ala to increase resistance to proteases, the 27th amino acid Met with Lys to increase oxidative stability, and the 20th and 24th amino acids Gln and the 28th amino acid Asn with Asp, Aln and Ser, respectively, to increase deamidation stability.

The ability of oxyntomodulin to act on both the GLP-1 receptor and the glucagon receptor offers promise in the development of a potential anti-obesity agent. However, the problem in the therapeutic use of oxyntomudulin is the extremely short half-life (8~12 min). The blood half-life of the dual agonist oxyntomodulin, although longer than that of native oxyntomodulin, still remains as short as 7 hours in vivo. Further, its administration dose is as high as several mg/kg. Thus, oxyntomodulin or its derivatives currently used suffer from the disadvantage that it has to be administered daily at a high dose due to short half-life and low efficacy. In case of protein drugs comprising such a peptide as an effective ingredient, it is necessary to administer the drug frequently through an injection so as to maintain the proper blood levels and titers, which is very painful to the patients. Therefore, the maintenance of high blood levels and proper efficacy is a prerequisite for the development of effective anti-obesity drugs.

Meanwhile, many attempts have been made to maximize drug efficacy by improving blood stability of a protein drug and maintaining high blood level thereof over a long period. In order for this, a method of chemically modifying the surface of a drug with a polymer such as polyethylene glycol (PEG) has been developed. However, the method has problems in that the higher the molecular weight of PEG, the lower its reactivity with a target protein, leading to a decrease in pegylation yield. Alternatively, International Patent Publication No. WO 02/46227 describes a fusion protein prepared by coupling a target protein with human blood albumin or an immunoglobulin region (Fc) via genetic recombination. U.S. Pat. No. 6,756,480 describes an Fc fusion protein prepared by coupling a parathyroid hormone (PTH) and an analog thereof with an Fc region. These methods can address the problems such as low pegylation yield and non-specificity, but they still have problems in that the effect of increasing the blood half-life is not noticeable as expected, and occasionally the titers are also low. In order to maximize the effect of increasing blood half-life, various kinds of peptide linkers are used, but an immune response may be possibly caused. Further, if a peptide having a disulfide bond is used, there is a high probability of misfolding.

In order to solve these problems, the present inventors have suggested a long-acting protein conjugate in which a physiologically active polypeptide and an immunoglobulin Fc fragment are covalently linked to each other via a non-peptide linker, thereby improving blood stability while maintaining a loss of drug activity (Korean Patent No. 10-0725315). Particularly, a long-acting exendin-4 conjugate in which exendin-4 or its derivative is covalently linked to an immunoglobulin Fc fragment via a non-peptide linker showed prolonged in vivo durability (Korean Patent Laid-Open Publication No. 10-2008-0064750).

Further, the present inventors have tried to apply the long-acting exendin-4 conjugate to the development of anti-obesity drugs with improved in vivo durability and stability. In this regard, the long-acting exendin-4 conjugate (once a week) was administered in combination with native glucagon (once a day) to simultaneously stimulate both the GLP-1 receptor and the glucagon receptor. When administered in combination with native glucagon, the long-acting exendin-4 brought about exceptional weight loss, compared to when administered alone. However, said co-administration caused severe fluctuation in blood glucose level, showing toxicity in test animals.

The present inventors have therefore endeavored to develop a method of increasing blood half-life of glucagon while maintaining in vivo activity thereof, and contrived a novel long-acting glucagon conjugate in which glucagon or its derivative is covalently linked to a polymer carrier such as an immunoglobulin Fc fragment via a non-peptide linker. The long-acting glucagon conjugate of the present invention shows improved in vivo durability and stability. Thus, when used in combination with an anti-obesity drug, the long-acting glucagon conjugate of the present invention can efficiently reduce body weight and food intake at a significantly low dose. Further, such co-administration exhibits better drug compliance without causing severe fluctuation in blood glucose level. Accordingly, the long-acting glucagon conjugate of the present invention can be effectively used for the prevention and treatment of obesity.

DISCLOSURE

Technical Problem

It is therefore an object of the present invention to provide a long-acting glucagon conjugate with improved in vivo durability and stability.

It is another object of the present invention to provide a method for preparing the long-acting glucagon conjugate.

It is a further object of the present invention to provide a pharmaceutical composition for the prevention and treatment of obesity, comprising the long-acting glucagon conjugate as an effective ingredient.

It is still a further object of the present invention to provide a method for preventing or treating obesity, comprising administering the pharmaceutical composition to a subject in need thereof.

It is still another object of the present invention to provide a use of the long-acting glucagon conjugate for the manufacture of a medicament for the prevention or treatment of obesity.

Technical Solution

In accordance with an aspect thereof, the present invention provides a novel long-acting glucagon conjugate in which glucagon or its derivative is covalently linked to a polymer carrier via a non-peptide linker.

As used herein, the term "glucagon" refers to a polypeptide hormone which is synthesized and secreted from alpha cells (α-cells) of the islets of Langerhans, consisting of 29 amino acids of SEQ ID NO: 1. Glucagon helps maintain the level of glucose in the blood. Glucagon signals the liver to break down glycogen to glucose, which is released into the blood stream. Further, glucagon stimulates the secretion of insulin, which allows glucose to be taken up and used by insulin-dependent tissues. Thus, glucagon and insulin are part of a feedback system that keeps blood glucose levels at a stable level.

The term "glucagon derivative" as used herein refers to a substance that binds to an glucagon receptor and elicits the same biological activity as that of glucagon. The glucagon derivative has an amino acid sequence which shares at least 80% homology with native glucagon, and may include a chemical substitution, deletion or modification at some amino acid residues. The glucagon derivative suitable for the present invention may be selected from the group consisting of agonists, derivatives, fragments and variants of native glucagon, and a combination thereof.

As used herein, the term "glucagon agonist" refers to a substance capable of binding to a glucagon receptor and showing the same physiological activity as that of glucagon, irrespective of the structure of glucagon.

The term "glucagon derivative" as used herein refers to a peptide showing glucagon activity, which has an amino acid sequence at least 80% identical to that of native glucagon and may include a chemical substitution (e.g., alpha-methylation, alpha-hydroxylation), deletion (e.g., deamination) or modification (e.g., N-methylation) at some amino acid residues.

As used herein, the term "glucagon fragment" refers to a peptide having glucagon activity, in which at least one amino acid is added to or deleted from the N- or C-terminal end of native glucagon. The glucagon peptide may be a peptide in which a non-naturally occurring amino acid (e.g., D-amino acid) is added thereto.

As used herein, the term "glucagon variant" refers to a peptide having glucagon activity, in which at least one amino acid sequence is different from that of native glucagon.

Preferably, the glucagon derivative of the present invention can be prepared by the substitution, deletion or modification of at least one N-terminal amino acid of native glucagon and can be selected from the group consisting of peptides having glucagon activity, and fragments and variants thereof. More preferably, the glucagon derivative can be a peptide in which an alpha-carbon of the first N-terminal amino acid histidine of native glucagon or an amine group attached thereto may be substituted, modified or deleted. Most preferably, the glucagon derivative of the present invention can be selected from the group consisting of a peptide in which the N-terminal amine group of native glucagon is deleted; a peptide in which the N-terminal amine group thereof is substituted with a hydroxyl group; a peptide in which the N-terminal amine group thereof is modified with two methyl groups; and a peptide in which the alpha-carbon of the N-terminal histidine thereof and the amine group attached thereto are deleted.

The glucagon derivatives suitable for the present invention can be represented by the following Formulae 1 to 4.

<Formula 1>

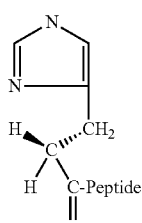

Des-amino-histidyl (DA)

<Formula 2>

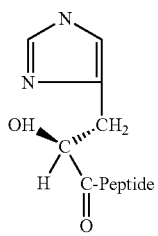

Beta-hydroxy-imidazopropionyl (HY)

<Formula 3>

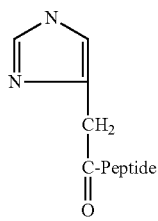

Imidazoacetyl (CA)

<Formula 4>

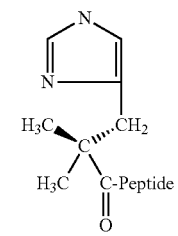

Dimethyl-histidyl (DM)

wherein, "Peptide" represents native glucagon.

The glucagon derivative of Formula 1 is des-amino-histidyl glucagon (hereinafter, referred to as "DA-glucagon") in which the N-terminal amine group of native glucagon is deleted.

The glucagon derivative of Formula 2 is beta-hydroxy-imidazopropionyl glucagon (hereinafter, referred to as "HY-glucagon") in which the N-terminal amine group of native glucagon is substituted with a hydroxyl group.

The glucagon derivative of Formula 3 is dimethyl histidyl glucagon (hereinafter, referred to as "DM-glucagon") in which the N-terminal amine group of native glucagon is modified with two methyl groups.

The glucagon derivative of Formula 4 is imidazoacetyl glucagon (hereinafter, referred to as "CA-glucagon") in which the alpha-carbon of the N-terminal histidine of native glucagon and the amine group attached thereto are deleted.

As used herein, the term "long-acting glucagon conjugate" refers to a glucagon or a glucagon derivative covalently linked to a polymer carrier via a non-peptide linker, which has a prolonged blood half-life and an improved in vivo activity. The long-acting glucagon conjugate of the present invention has a blood half-life increased by 10% or more, preferably 50% or more, as compared with native glucagon or its derivative.

The term "non-peptide linker" as used herein refers to a biocompatible polymer including two or more repeating units that are linked to each other by any covalent bond except a peptide bond. Since the non-peptide linker suitable for the present invention includes functional groups at their both ends, glucagon or its derivatives can be covalently linked to one end thereof and a polymer carrier can be linked to the other end thereof.

The non-peptide linker suitable for the present invention may include polyethylene glycol (PEG), polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic glycolic acid), lipid polymers, chitins, hyaluronic acid and so on, but are not limited thereto. Preferably, polyethylene glycol can be used as a non-peptide linker.

The peptide linker used in a fusion protein obtained by a conventional inframe fusion method has drawbacks that it is easily cleaved in vivo by a proteolytic enzyme, and thus a sufficient effect of increasing a blood half-life of the peptide drug cannot be obtained as expected. However, the present invention uses a non-peptide linker having resistance to the proteolytic enzyme, which results in maintaining a blood half-life of the peptide drug at a high level. Therefore, there is no limitation to the kind of non-peptide linkers as long as they are resistant to proteolytic enzyme activities.

Preferably, the non-peptide linker suitable for the present invention has a molecular weight ranging from 1 to 100 kDa, more preferably, 1 to 20 kDa. Also, the non-peptide linker of the present invention may be one kind of a polymer or a combination of different kinds of polymers.

The non-peptide linker suitable for the present invention has functional groups at both ends thereof. The functional group of the non-peptide linker is preferably selected from the group consisting of aldehyde, propionaldehyde, butylaldehyde, maleimide and succinimide derivatives. The examples of the succinimide derivatives suitable for the present invention may include succinimidyl propionate, hydroxy succinimidyl, succinimidyl carboxymethyl and succinimidyl carbonate, but are not limited thereto. In particular, when the non-peptide linker has an aldehyde group at both ends, it is effective in linking glucagon or its derivatives and a polymer carrier to both ends, respectively, with minimizing non-specific reactions. Further, the linking through the aldehyde group is much more stable that through an amide group.

The functional groups at both ends of the non-peptide linker may be the same or different. For example, the non-peptide linker may include a maleimide group at one end and an aldehyde group, a propionaldehyde group or a butylaldehyde group at the other end. When PEG with hydroxy groups at both ends is used as a non-peptide linker, the hydroxy groups may be activated to various functional groups by known chemical reactions. Alternatively, PEGs with modified functional groups at both ends that are commercially available may be used.

The non-peptide linker of the present invention can be linked to various sites of glucagon or its derivatives, and the resulting products show different activities depending on the site linked between them. For example, the non-peptide linker can be linked to the N-terminal end of the peptide or other sites including the C-terminal end thereof except the N-terminal end, leading to the difference in in vitro activities. The aldehyde group of the non-peptide linker can selectively react with glucagon or its derivatives at low pH, while at high pH (e.g., pH 9.0), it can form a covalent bonding with a lysine residue of glucagon or its derivatives. Such a pegylation is carried out with varying pH conditions, the resulting isomers can be separated from the reaction mixture by ion-exchange column chromatography.

When the non-peptide linker is linked to the other site of the peptide except the N-terminal end where it is important to in vivo activities, a thiol group is introduced into the amino acid residue of the peptide to be modified, which makes it possible to form a covalent bonding between the thiol group of the peptide and the maleimide group of the non-peptide linker.

Further, when the non-peptide linker is linked to the other site of the peptide except the N-terminal end where it is important to in vivo activities, an amine group is introduced into the amino acid residue of the peptide to be modified, which makes it possible to form a covalent bonding between the amine group of the peptide and the aldehyde group of the non-peptide linker.

The aldehyde group of the non-peptide linker can react with an amino group present at the N-terminal end and 12th lysine residue of glucagon. Here, a modified form of the peptide can be used to selectively increase reaction yield. For example, only one amine group of the peptide can be retained on a desired site by blocking the N-terminal end thereof, substituting a lysine residue with other amino acids, introducing an amine group into the C-terminal end or the like. Through such a modification, it is possible to increase the yield of pegylation and coupling reaction yield between the non-peptide linker and peptide. The N-terminal end of the peptide may be blocked by various alkylation methods such as dimethylation, methylation, deamination and acetylation, but are not limited thereto.

In a preferred embodiment of the present invention, the long-acting glucagon conjugate has a structure where a polymer carrier covalently linked to an amine group of native glucagon or its derivative rather than the N-terminal end thereof via a non-peptide linker, while maintaining binding ability to the glucagon receptor.

The term "polymer carrier" as used herein refers to a substance to be linked to a drug so as to increase, decrease or eliminate the physiological activity of the drug. However, with respect to the object of the present invention, the polymer carrier is to enhance the in vivo stability of glucagon or its derivative while minimizing the decrease in physiological activity thereof. The polymer carrier suitable for the present invention may include polyethylene glycol (PEG), polyamino acids, albumin, gelatin, immunoglobulin fragments, dextran, fatty acids, polysaccharides and polymers, but are not limited thereto. It is preferable to use an immunoglobulin Fc fragment as a polymer carrier.

The immunoglobulin Fc fragment is safe for use as a drug carrier because it is a biodegradable polypeptide being metabolized in the body. Also, the immunoglobulin Fc fragment has a relatively low molecular weight compared to a whole immunoglobulin molecule, thus being advantageous in the preparation, purification and yield of conjugates. Since the immunoglobulin Fc fragment does not contain the Fab fragment, it shows significantly increased homogeneity while decreasing the cause of antigenecity.

The term "immunoglobulin (IgG) Fc fragment" as used herein refers to a protein that contains the heavy-chain constant region 2 ($C_{H2}$) and the heavy-chain constant region 3 ($C_{H3}$) of an immunoglobulin, and not the variable regions of the heavy and light chains, the heavy-chain constant region 1 ($C_{H1}$) and the light-chain constant region 1 ($C_{L1}$) of the immunoglobulin. It may further include a hinge region at the heavy-chain constant region. Further, the IgG Fc fragment of the present invention may be an expanded form thereof containing the heavy-chain constant region 1 ($C_{H1}$) and/or the light-chain constant region 1 ($C_{L1}$) in whole or in part, except the variable regions of the heavy and light chains, so long as it has a physiological function substantially similar to or better than the native form. In addition, the IgG Fc fragment may be a fragment in which a relatively long portion of the amino acid sequence corresponding to $C_{H2}$ and/or $C_{H3}$ domains. That is, the IgG Fc fragment of the present invention may comprise 1) a $C_{H1}$ domain, a $C_{H2}$ domain, a $C_{H3}$ domain and a $C_{H4}$ domain, 2) a $C_{H1}$ domain and a $C_{H2}$ domain, 3) a $C_{H1}$ domain and a $C_{H3}$ domain, 4) a $C_{H2}$ domain and a $C_{H3}$ domain, 5) a combination of one or more domains described above and an IgG hinge region (or a portion of the hinge region), and 6) a dimer of each domain of the heavy-chain constant region and the light-chain constant region.

The IgG Fc fragment of the present invention may include a native amino acid sequence and sequence derivatives (mutants) thereof. The term "sequence derivatives" as used herein refers to a sequence that is different from the native amino acid sequence due to deletion, insertion, non-conservative or conservative substitution or combinations thereof of one or more amino acid residues. For example, in the case of an IgG Fc, amino acid residues at positions 214 to 238, 297 to 299, 318 to 322, or 327 to 331 known to be important for binding may be used as a suitable target site for such a modification. Further, such sequence derivatives can be prepared by removing a site capable of forming a disulfide bond, eliminating certain amino acid residues from the N-terminal end of a native Fc, or introducing a methionine residue into the N-terminal end thereof. Furthermore, to remove effector functions, it is possible to delete a complement-binding site (e.g., C1q-binding site) or an ADCC (antibody dependent cell mediated cytotoxicity) site. The preparation of such sequence derivatives is well known in the art, for example, in International Patent Publication Nos. WO 97/34631 and WO 96/32478.

Amino acid exchanges in proteins and peptides, which do not generally alter the activity of the proteins, or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

In addition, the Fc fragment, if desired, may be modified by phosphorylation, sulfation, acrylation, glycosylation, methylation, farnesylation, acetylation, amidation, and the like.

The aforementioned Fc derivatives are derivatives that have a biological activity identical to the Fc fragment of the present invention or improved structural stability, for example, against heat, pH, or the like.

In addition, these Fc fragments may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc fragments, and pepsin treatment results in the production of pFc' and F(ab')$_2$ fragments. These fragments may be subjected, for example, to size exclusion chromatography to isolate Fc or pFc'. Preferably, a human-derived Fc fragment is a recombinant immunoglobulin Fc fragment that is obtained from a microorganism.

In addition, the immunoglobulin Fc fragment of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc fragment results in a sharp decrease in binding affinity to the Clq part of the first complement component C1 and a decrease or loss in antibody-dependent cell-mediated cytotoxicity (ADCC) or complement-dependent cytotoxicity (CDC), thereby not inducing unnecessary immune responses in vivo. In this regard, an immunoglobulin Fc fragment in a deglycosylated or aglycosylated form may be more suitable to the object of the present invention as a drug carrier.

As used herein, the term "deglycosylation" refers to enzymatically remove sugar moieties from an Fc fragment, and the term "aglycosylation" means that an Fc fragment is produced in an unglycosylated form by a prokaryote, preferably *E. coli*.

On the other hand, the immunoglobulin Fc fragment may be derived from humans or other animals including cows, goats, swine, mice, rabbits, hamsters, rats and guinea pigs, and preferably humans. In addition, the immunoglobulin Fc fragment may be an Fc fragment that is derived from IgG, IgA, IgD, IgE and IgM, or that is made by combinations thereof or hybrids thereof. Preferably, it is derived from IgG or IgM, which is among the most abundant proteins in human blood, and most preferably from IgG, which is known to enhance the half-lives of ligand-binding proteins.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected-from the group consisting of IgG1 Fc, IgG2 Fc, IgG3 Fc and IgG4 Fc fragments.

As used herein, the term "hybrid" means that sequences encoding two or more immunoglobulin Fc fragments of different origin are present in a single-chain immunoglobulin Fc fragment. In the present invention, various types of hybrids are possible. That is, domain hybrids may be composed of one to four domains selected from the group consisting of $C_{H4}$, $C_{H2}$, $C_{H3}$ and $C_{H4}$ of IgG1 Fc, IgG2 Fc, IgG3 Fc and IgG4 Fc, and may include the hinge region.

On the other hand, IgG is divided into IgG1, IgG2, IgG3 and IgG4 subclasses, and the present invention includes combinations and hybrids thereof. Preferred are IgG2 and IgG4 subclasses, and most preferred is the Fc fragment of IgG4 rarely having effector functions such as CDC (complement dependent cytotoxicity).

That is, as the drug carrier of the present invention, the most preferable immunoglobulin Fc fragment is a human IgG4-derived non-glycosylated Fc fragment. The human-derived Fc fragment is more preferable than a non-human derived Fc fragment, which may act as an antigen in the human body and cause undesirable immune responses such as the production of a new antibody against the antigen.

In a preferred embodiment, the long-acting glucagon conjugate according to the present invention may be represented by the following Formula 5:

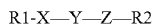   <Formula 5> wherein, R1 is selected from the group consisting of histidine (His), des-amino-histidyl, N-dimethyl-histidyl, beta-hydroxy imidazopropyl and 4-imidazoacetyl;

R2 is selected from the group consisting of —NH2, —OH and lysine (Lys);

X is SQGTFTSDYSKYLDSRRAQDFVQWLMNT (SEQ ID NO: 3);

Y is polyethylene glycol (PEG);

Z is an immunoglobulin Fc fragment.

In the long-acting glucagon conjugate according to a preferred embodiment of the present invention, both ends of PEG are covalently linked to the 12th lysine (Lys12) of CA-glucagon (i.e., R1 is 4-imidazoacetyl in Formula 5) and the N-terminal end of an immunoglobulin Fc fragment, respectively.

In accordance with another aspect, the present invention provides a method for preparing the long-acting glucagon conjugate.

The method of the present invention comprises:

1) reacting a non-peptide linker having a functional group at both ends with native glucagon or its derivative;

2) separating from the reaction mixture of step 1) a complex in which the native glucagon or its derivative is covalently linked to one end of the non-peptide linker;

3) reacting the complex separated in step 2) with a polymer carrier; and 4) separating from the reaction mixture of step 3) a long-acting glucagon conjugate in which the non-peptide linker is covalently linked at one end to the native glucagon or its derivative and at the other end to the polymer carrier.

As used herein, the term "complex" refers to an intermediate in which native glucagon or its derivative is covalently linked to one end of the non-peptide linker. According to the method of the present invention, the complex will be subjected to form a covalent bond between the other end of the non-peptide linker and a polymer carrier.

In step 1), glucagon or its derivative reacts with a non-peptide linker so as to form a complex between them. In this step, native glucagon having the amino acid sequence of SEQ ID NO: 1 or its derivative can be used. Examples of the derivatives may include: DA-glucagon of Formula 1 in which the N-terminal amine group of native glucagon is deleted; HY-glucagon of Formula 2 in which the N-terminal amine group thereof is substituted with a hydroxyl group; DM-glucagon of Formula 3 in which the N-terminal amine group thereof is modified with two methyl groups; and Ca-glucagon of Formula 4 in which the alpha-carbon of the N-terminal histidine thereof and the amine group attached thereto are deleted.

The non-peptide linker used in step 1) has a functional group at both ends thereof. The functional group of the non-peptide linker is preferably selected from the group consisting of aldehyde, propionaldehyde, butylaldehyde, maleimide and succinimide derivatives. Examples of the succinimide derivatives suitable for the present invention may include succinimidyl propionate, hydroxy succinimidyl, succinimidyl carboxymethyl and succinimidyl carbonate, but are not limited thereto. The functional groups at both ends of the non-peptide linker may be the same or different. Preferably, PEG with an aldehyde group at both ends is used as a non-peptide linker. Such an aldehyde group of the non-peptide linker is effective for linking the glucagon or its derivative and polymer carrier to both ends thereof, respectively, while minimizing non-specific reactions. Further, the linking through the aldehyde group is much more stable than through an amide group.

In step 1), the non-peptide linker may be covalently linked to an amino acid residue other than the N-terminal end of native glucagon or its derivative, preferably to the 12th lysine residue. To selectively link the non-peptide linker to an amino acid residue other than the N-terminal end, preferably to the 12th lysine residue in step 1), glucagon or its derivative is reacted with the non-peptide linker at pH ranging from 7.5 to 10.0, preferably at pH 9.0. Here, the molar ratio between glucagon or its derivative and the non-peptide linker may range from 1:5 to 1:50, preferably 1:20 to 1:30. In step 1), the use of glucagon derivative whose N-terminal end is deleted or protected is effective for preventing the non-peptide linker from linking to the N-terminal end thereof.

The reaction of step 1) may be performed optionally in the presence of a reducing agent depending on the kind of the functional group at both ends of the non-peptide linker. Preferred examples of the reducing agent may include sodium cyanoborohydride (NaCNBH$_3$), sodium borohydride, dimethylamine borate and pyridine borate, but are not limited thereto.

In step 2), a glucagon-non-peptide linker complex in which glucagon or its derivative is covalently linked to one end of the non-peptide linker is separated from the reaction mixture of step 1). The complex separated in step 2) has a structure of glucagon-non-peptide linker. With the consideration of desired properties of the resulting product such as purity, molecular weight and charge, the separation step can be performed according to a proper method conventionally used for protein isolation. For example, size exclusion chromatography or ion-exchange chromatography may be employed. If necessary, it is possible to employ a plurality of different methods, so as to separate the resulting product at higher purity.

In step 3), the complex of glucagon-non-peptide linker separated in step 2) reacts with a polymer carrier, to link the polymer carrier to the exposed end of the non-peptide linker by a covalent bond. The polymer carrier useful in this step may be selected from the group consisting of polyethylene glycol (PEG), polyamino acids, albumin, gelatin, immunoglobulin fragments, dextran, fatty acids, polysaccharides and macromolecule polymers, but are not limited thereto. Preferably, an immunoglobulin (IgG) Fc fragment is used as a polymer carrier.

In this step, the complex and the polymer carrier are reacted at a molar ratio ranging from 1:2 to 1:10, preferably 1:4 to 1:8, at pH ranging from 5.0 to 8.0, preferably at pH 6.0. If necessary, depending on the kind of the functional group at both ends of the non-peptide linker, the reaction may be conducted in the presence of a reducing agent. Examples of the reducing agent may include sodium borohydride (NaCNBH$_3$), sodium borohydride, dimethylamine borate and pyridine borate, but are not limited thereto.

In step 4), the long-acting glucagon conjugate in which the non-peptide linker is covalently linked at one end thereof to glucagon or its derivative and at the other end thereof to the polymer carrier is separated from the reaction mixture of step 3). With the consideration of desired properties of the resulting product such as purity, molecular weight and charge, the separation step can be performed according to a proper method conventionally used for protein isolation. For example, size exclusion chromatography or ion-exchange chromatography may be employed. If necessary, it is possible to employ a plurality of different methods, so as to separate the resulting product at higher purity.

In a preferred embodiment, the preparation method of the present invention comprises:

1) reacting PEG having an aldehyde group at each end with a glucagon derivative of Formula 4 at pH 9.0;

2) separating from the reaction mixture of step 1) a glucagon derivative-PEG complex in which PEG is covalently linked at one end to the 12th lysine residue of the glucagon derivative;

3) reacting the glucagon derivative-PEG complex separated in step 2) with an immunoglobulin Fc fragment; and 4) separating from the reaction mixture of step 3) a long-acting glucagon conjugate in which PEG is covalently linked at one end to the glucagon derivative and at the other end to the immunoglobulin Fc fragment.

In accordance with a further aspect, the present invention provides a pharmaceutical composition for the prevention or treatment of obesity, comprising the long-acting glucagon conjugate as an effective ingredient.

As used herein, the term "obesity" refers to a medical condition or a disease in which excess body fat has accumulated due to an energy imbalance. The administration of the pharmaceutical composition according to the present invention can significantly reduce body weight and decrease food intake, leading to the prevention or treatment of obesity.

As used herein, the term "prevention" refers to any action resulting in suppression or delay of the onset of obesity thanks to the administration of the pharmaceutical composition according to the present invention.

As used herein, "treatment" refers to any action resulting in improvement in symptoms of obesity or the beneficial alteration from the administration of the composition according to the present invention.

Since the pharmaceutical composition of the present invention comprises the long-acting glucagon conjugate with a prolonged blood half-life and an improved in vivo durability and stability as an effective ingredient, it can considerably reduce the administration dose of the drug, exhibit improved drug compliance without fluctuation in the blood glucose level, and thereby, be effective for preventing and treating obesity.

The pharmaceutical composition of the present invention may further comprise an anti-obesity drug as an effective ingredient in addition to the long-acting glucagon conjugate of the present invention.

Examples of the anti-obesity drug suitable for the administration in combination with the long-acting glucagon conjugate of the present invention may include GLP-1 agonists, leptin agonists, DPP-IV inhibitors, Y5 receptor antagonists, melanin-concentrating hormone (MCH) antagonists, Y2/3 agonists, MC3/4 agonists, gastric/pancreatic lipase inhibitors, 5HT$_{2C}$ agonists, βA agonists, amylin agonists and ghrelin antagonists, but are not limited thereto.

Preferably, the pharmaceutical composition according to the present invention may further comprise the long-acting exendin-4 conjugate disclosed in Korean Patent Laid-Open Publication No. 10-2008-0064750 as an anti-obesity drug. The long-acting exendin-4 conjugate is composed of exendin-4 (GenBank Accession No. AAB22006, SEQ ID NO: 2) or its derivative and an immunoglobulin Fc fragment that are covalently linked to each other via a non-peptide linker. In a preferred embodiment, the exendin-4 derivative selected from the group consisting of a peptide in which the N-terminal amine group of native exendin-4 is deleted (DA-exendin- 4); a peptide in which the N-terminal amine group thereof is substituted with a hydroxyl group (HY-exendin-4); a peptide in which the N-terminal amine group thereof is modified with two methyl groups (DM-exendin-4); and a peptide in which the alpha-carbon of the N-terminal histidine thereof and the amine group attached thereto are deleted (CA-exendin-4) is covalently linked to an immunoglobulin Fc fragment via a non-peptide linker.

When administered in combination with an anti-obesity drug, the long-acting glucagon conjugate of the present invention shows a synergistic effect on the loss of body weight and decrease in food intake, as compared with the administration of the long-acting glucagon conjugation alone. In particular, when the long-acting glucagon conjugate of the present invention is administered in combination with the long-acting exendin-4 conjugate, the long-acting glucagon conjugate acts on the glucagon receptor, and simultaneously, the anti-obesity drug acts on the GLP-1 receptor, thereby more efficiently reducing body weight and decreasing food intake. Since the co-administration of the long-acting peptide conjugates can significantly increase blood half-life and in vivo durability, show more stable fluctuation in blood glucose level, and considerably reduce the dose thereof, the pharmaceutical composition of the present invention is very effective for the prevention and treatment of obesity.

In a preferred embodiment, the long-acting conjugate of the present invention is administered in combination with the long-acting exendin-4 conjugate to diet-induced obesity (DIO) mice, followed by monitoring for changes in their body weight, food intake amount and blood glucose level. As a result, it has been found that the co-administration of the drugs significantly reduces body weight, effectively suppresses food intake and shows more stable fluctuation in blood glucose level, as compared to when either of the drugs is administered (see FIGS. 1 to 3). On the other hand, when native glucagon is administered in combination with the long-acting exendin-4 conjugate to DIO mice, the reduction of body weight is observed, but there is severe fluctuation in the blood glucose level (see FIGS. 4 and 5). These results demonstrate that only when both glucagon and exendin-4 are in the form of a long-acting conjugate, it can be expected to bring about a synergistic effect on the loss of body weight and decrease in the amount of food intake without causing any side-effects such as fluctuation in blood glucose level, and can significantly reduce the dose of the drugs due to their in vivo durability and stability.

The pharmaceutical composition of the present invention can further comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent and a perfume. For injectable administration, the pharmaceutically acceptable carrier may include a buffering agent, a preserving agent, an analgesic, a solubilizer, an isotonic agent and a stabilizer. For topical administration, the pharmaceutically acceptable carrier may include a base, an excipient, a lubricant, and a preserving agent.

The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable administration, the pharmaceutical composition may be formulated into an ampule as a single-dose dosage form or a unit dosage form, such as a multidose container. The pharmaceutical composition may be also formulated into solutions, suspensions, tablets, pills, capsules and long-acting preparations.

On the other hand, examples of the carrier, excipient and diluent suitable for the pharmaceutical composition of the present invention may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate and mineral oils. In addition, the pharmaceutical composition of the present invention may further include fillers, anti-coagulating agents, lubricants, humectants, perfumes and antiseptics.

The pharmaceutical composition of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but are not limited thereto.

However, since peptides are digested upon oral administration, the effective ingredient of the pharmaceutical composition for oral administration should be coated or formulated for protection against degradation in the stomach. Preferably, the pharmaceutical composition of the present invention may be administered in an injectable form. In addition, the pharmaceutical composition of the present invention may be administered using a certain apparatus capable of transporting the effective ingredient into a target cell.

The administration frequency and dose of the pharmaceutical composition of the present invention can be determined by several related factors including the types of diseases to be treated, administration routes, the patient's age, gender, weight and severity of the illness, as well as by the types of the drug as an effective ingredient. For example, when used in combination with an anti-obesity drug, the long-acting glucagon conjugate of the present invention can be administered weekly at a dose of 10 to 4000 µg/kg, preferably 50 to 2000 µg/kg, and the long-acting exendin-4 conjugate, weekly at a dose of 5 to 100 µg/kg, preferably 10 to 50 µg/kg. However, the dose may be increased or decreased according to the route of administration, the severity of disease, and patient's sex, weight and age, and thus in no way limits the scope of the present invention. Showing excellent in vivo persistency and titer, the pharmaceutical composition of the present invention may be remarkably decreased in administration frequency. Since the pharmaceutical composition of the present invention has excellent in vivo durability and stability with prolonged blood half-life, it can remarkably reduce the administration frequency and dose of the drugs.

In accordance with still a further aspect, the present invention provides a method for preventing or treating obesity, comprising administering the long-acting glucagon conjugate in a therapeutically effective amount to a subject in need thereof. In this regard, the long-acting glucagon conjugate of the present invention can be administered in combination with an anti-obesity drug.

The anti-obesity drug that can be administered in combination with the long-acting glucagon conjugate is preferably the long-acting exendin-4 conjugate disclosed in Korean Patent Laid-Open Publication No. 10-2008-0064750. The long-acting exendin-4 conjugate is composed of exendin-4 or its derivative and an immunoglobulin Fc fragment which are covalently held together via a non-peptide linker. In a preferred long-acting exendin-4 conjugate, an exendin-4 derivative selected from among a derivative prepared by deleting the N-terminal amine group of exendin-4 (DA-exendin-4), a derivative prepared by substituting the N-terminal amine group with a hydroxyl group (HY-exendin-4), a derivative prepared by modifying the N-terminal amine group with two methyl groups (DM-exendin-4), and a derivative prepared by deleting the alpha-carbon of the N-terminal histidine of exendin-4 and the amine group attached to the alpha-carbon (CA-exendin-4), is covalently linked to an immunoglobulin Fc fragment via a non-peptide linker, but the present invention is not limited thereto.

As used herein, the term "administration" refers to introduction of an effective ingredient into a patient in a suitable manner. As long as it allows the effective ingredient to reach a target tissue, any administration may be taken. Examples of the administration route include intraperitoneal, intravenous, intramuscular, subcutaneous, interdermal, oral, local, intranasal, intrapulmonary and intrarectal administration, but are not limited thereto. However, since peptides are digested upon oral administration, the effective ingredient of a composition for oral administration should be coated or formulated for protection against degradation in the stomach. Preferably, the effective ingredient may be formulated into an injection. In addition, the long-acting conjugate may be administered with the aid of any device that helps transmit the effective ingredient into target cells.

Examples of the subject to be treated include humans, apes, cow, horses, sheep, pigs, chickens, turkeys, quails, cats, dogs, mice, rats, rabbits and guinea pigs, but are not limited thereto. Preferred are mammals. More preferred are humans.

The term "therapeutically effective amount" as used in the context of the effective ingredient refers to an amount sufficient for preventing or treating a disease, that is, obesity in a reasonable benefit/risk ratio so as to be applicable to medical treatment.

When administered in combination with an anti-obesity drug, the long-acting glucagon conjugate of the present invention acts on the glucagon receptor, and simultaneously, the anti-obesity drug acts on the GLP-1 receptor, thereby inducing synergistic effect on the loss of body weight and decrease in food intake without causing any side-effects such as fluctuation in blood glucose level. Accordingly, the long-acting peptide conjugate of the present invention is very effective for the prevention and treatment of obesity.

Advantageous Effects

The long-acting glucagon conjugate of the present invention shows a prolonged blood half-life and an improved in vivo durability and stability. Thus, when used in combination with an anti-obesity drug, the long-acting glucagon conjugate of the present invention can be administered at a remarkably low dose and exhibit an improvement in drug compliance without fluctuation in blood glucose level. Accordingly, the long-acting glucagon conjugate of the present invention can be effectively used for preventing or treating obesity.

MODE FOR INVENTION

Figure 1:
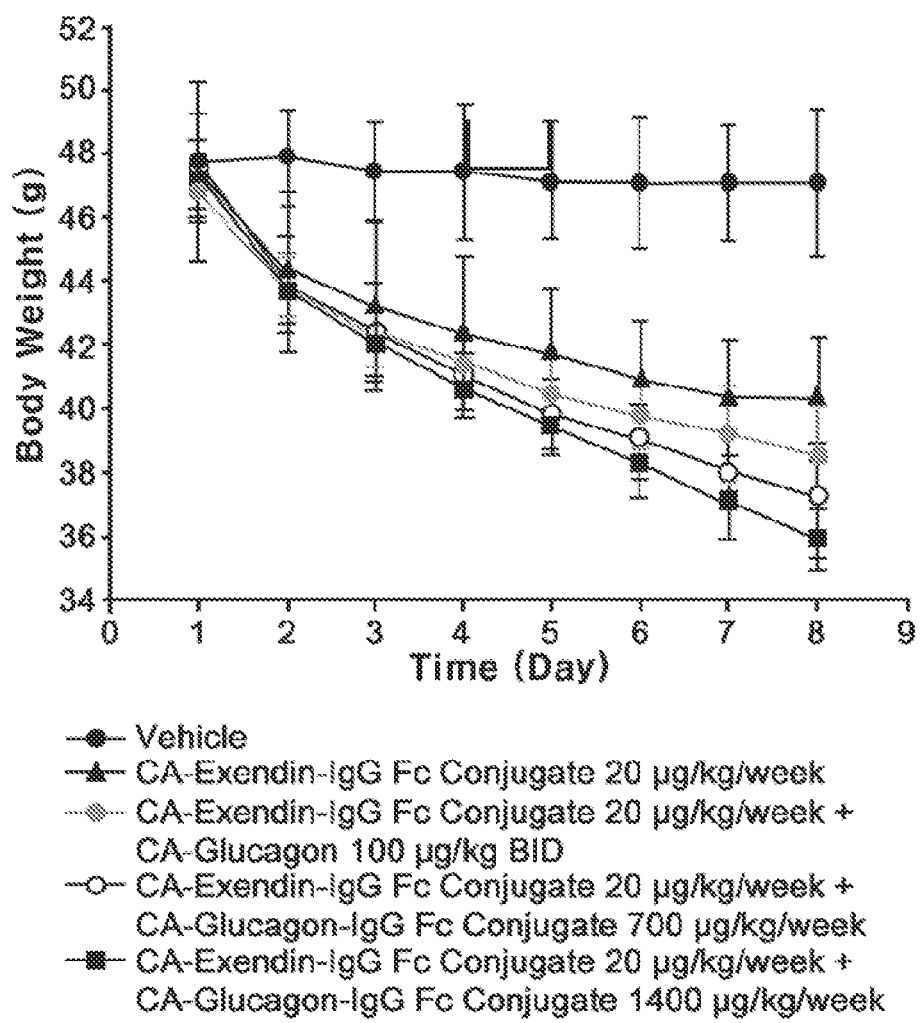
FIG. 1 is a graph showing changes in body weight of DIO (Diet-Induced Obesity) mice for 8 days after the co-administration of a long-acting CA-glucagon conjugate with a long-acting CA-exendin-4 conjugate.

A better understanding of the present invention may be obtained through the following examples which are set forth to illustrate, but are not to be construed as limiting the present invention.

Example 1

Preparation of Imidazo-Acetyl Glucagon-Immunoglobulin Fc Conjugate

Imidazo-acetyl glucagon (CA-glucagon, AP, U.S.A.) was reacted with 3.4K PropionALD(2) PEG (PEG having a propionaldehyde group at both ends, IDB Inc., Korea), so as to pegylate the 12th lysine residue (Lys12) of the CA-glucagon. Here, the molar ratio of CA-glucagon and PEG was 1:30, and the reaction was performed at room temperature for 3 hours, with a peptide concentration of 3 mg/mL. Further, the reaction was carried out in 100 mM Na-borate buffer (pH 9.0) in the presence of 20 mM SCB as a reducing agent. After the reaction was completed, the resulting product, CA-glucagon-PEG complex was purified by chromatography using a SOURCE S column (XK 16 ml, GE Healthcare) under the following conditions.

Column: SOURCE S (XK 16 ml, GE Healthcare)
Flow rate: 2.0 ml/min
Gradient: eluting for 50 min with eluent A 0%→eluent B 50% (A: 20 mM citric acid, pH 3.0, B: A+1 M KCl)

The CA-glucagon-PEG complex purified above was mixed with an immunoglobulin (IgG) Fc fragment (Korean Patent No. 10-725315) at a molar ratio of 1:8, followed by reacting them at 4° C. for 20 hours, with a peptide concentration of 20 mg/ml. At this time, the reaction was performed in 100 mM K—P buffer (pH 6.0) in the presence of 20 mM SCB as a reducing agent. After the reaction was completed, the reaction mixture was subjected to two-step chromagraphy using a SOURCE Phe column (HR 16 ml, GE Healthcare) and a SOURCE Q column (XK 16 ml, GE Healthcare) under the following conditions.

Column: SOURCE Phe (HR 16 ml, GE Healthcare)
Flow rate: 7.0 ml/min
Gradient: eluting for 60 min with eluent A 100%→0% (A: 20 mM Tris, pH 7.5+2 M NaCl)
Column: SOURCE Q (XK 16 ml, GE Healthcare)
Flow rate: 2.0 ml/min
Gradient: eluting for 70 min with eluent A 0%→eluent B 20% (A: 20 mM Tris, pH 9.0, B: A+1 M NaCl)

First, the SOURCE Phe column was used to remove a large amount of IgG Fc which had not participated in the reaction. Using 20 mM Tris (pH 7.5) and 1M NaCl with salt gradients, the IgG Fc having relatively weak binding affinity was eluted earlier, and then the Ca-glucagon-PEG-Fc conjugate was eluted. The IgG Fc was removed to some degree through this first purification procedure, but the IgG Fc and CA-glucagon-PEG-Fc conjugate could not be completely separated from each other because of their similar binding affinities. For the second purification process, difference in hydrophobicity between them was utilized. Using 20 mM Tris (pH 9.0), the first purified samples were coupled to the SOURCE Q column. The sample was then eluted using 1 M NaCl with salt gradients. In the SOURCE Q column, the IgG Fc having weak binding affinity was eluted earlier, and then the CA-glucagon-PEG-Fc conjugate having strong binding affinity was eluted. As a result of reverse-phase HPLC analysis, the CA-glucagon-PEG-Fc conjugate purified above showed a purity of 95.8%.

Example 2

Preparation of Imidazo-Acetyl Exendin-4-Immunoglobulin Fc Conjugate

Imidazo-acetyl exendin-4 (CA-exendin-4, AP, U.S.A.) was reacted with 3.4K PropionALD(2) PEG (PEG having a propionaldehyde group at both ends, IDB Inc., Korea), so as to pegylate the 27th lysine residue (Lys27) of the CA-exendin-4. Here, the molar ratio of CA-exendin-4 and PEG was 1:30, and the reaction was performed at 4° C. for 12 hours, with a peptide concentration of 3 mg/mL. Further, the reaction was carried out in 100 mM Na-borate buffer (pH 7.5) in the presence of 20 mM SCB as a reducing agent. After the reaction was completed, the resulting product, CA-exendin-4-PEG complex was purified by chromatography using a SOURCE Q column (XK 16 ml, GE Healthcare) and a SOURCE S column (XK 16 ml, GE Healthcare) under the following conditions.

Column: SOURCE Q (XK 16 ml, GE Healthcare)
Flow rate: 2.0 ml/min
Gradient: Eluting for 70 min with eluent A 0%→eluent B 20% (A: 20 mM Tris, pH 9.0, B: A+1 M NaCl)
Column: SOURCE S (XK 16 ml, GE Healthcare)
Flow rate: 2.0 ml/min
Gradient: Eluting for 50 min with eluent A 0%→eluent B 50% (A: 20 mM citric acid, pH 3.0, B: A+1 M KCl)

In detail, a mono-pegylated peptide was primarily purified through the SOURCE Q column, followed by the separation of isomers through the SOURCE S column. A peak for N-terminal pegylated peptides was first eluted, and then two peaks for Lys-pegylated peptides were eluted. Peptide mapping of the two Lys-pegylated peaks showed that the earlier eluted fraction was the Lys12-pegylated complex, and the later eluted fraction was the Lys27-pegylated complex.

The Lys27-pegylated CA-exendin-4-PEG complex thus obtained was mixed with an immunoglobulin Fc fragment (Korean Patent No. 10-725315) at a molar ratio of 1:8, followed by reacting them at 4° C. for 20 hours, with a peptide concentration of 20 mg/ml. At this time, the reaction was performed in 100 mM K—P buffer (pH 6.0) in the presence of 20 mM SCB as a reducing agent. After the reaction was completed, the reaction mixture was subjected to two-step chromagraphy using a SOURCE Q column (XK 16 ml, GE Healthcare) and a SQOUCE ISO column (HR 16 ml, GE Healthcare) under the following conditions.

Column: SOURCE Q (XK 16 ml, GE Healthcare)
Flow rate: 2.0 ml/min
Gradient: Eluting for 70 min with eluent A 0%→eluent B 20% (A: 20 mM Tris, pH 9.0, B: A+1 M NaCl)
Column: SOURCE ISO(HR 16 ml, GE Healthcare)
Flow rate: 7.0 ml/min
Gradient: Eluting for 60 min with eluent A 100%→0% 60 min (A: 20 mM Tris, pH 7.5+1.5 M ammonium sulfate)

First, the SOURCE Q column was used to remove a large amount of IgG Fc which had not participated in the reaction. Using 20 mM Tris (pH 7.5) and 1 M NaCl with salt gradients, the IgG Fc having relatively weak binding affinity was eluted earlier, and then the Ca-exendin-4-PEG-Fc conjugate was eluted. The IgG Fc was removed to some degree through this first purification procedure, but the IgG Fc and CA-exendin-4-PEG-Fc conjugate could not be completely separated from each other because of their similar binding affinities. For the second purification process, difference in hydrophobicity between them was utilized. Using 20 mM Tris (pH 9.0), the first purified samples were coupled to the SOURCE ISO column. The sample was then eluted using 1 M NaCl with salt gradients. In the SOURCE ISO column, the IgG Fc having weak binding affinity was eluted earlier, and then the CA-exendin-4-PEG-Fc conjugate having strong binding affinity was eluted. As a result of reverse-phase HPLC analysis, the CA-exendin-4-PEG-Fc conjugate purified above showed a purity of 91.6%.

Example 3

Synergistic Effect by Co-Administration of a Long-Acting Glucagon Conjugate with an Anti-Obesity Drug To confirm the synergistic effect upon the co-administration of the long-acting glucagon conjugate prepared in Example 1 with the long-acting exendin-4 conjugate prepared in Example 2, diet-induced obesity (DIO) mice were analyzed for changes in weight, food intake and blood glucose level.

Five-week-old C57BL/6 mice (Orient, Korea) were fed with a high-fat diet for 13 weeks, to thereby obtain diet-induced obesity (DIO) mice as a diabetic model. In detail, mice were divided into five groups, G1, G2, G3, G4 and G5 groups (5 mice/per group) according to body weight, and allowed to freely access the high-fat diet (D12492, Research Diets, Inc. New Brunswick, N.J.), with the high-fat diet exchanged every day with a fresh one. The mice in the five groups, which were 18 weeks old (50 g/head), were administered respectively with a vehicle as a control; CA-exendin-4-PEG-Fc conjugate (HM1 1260C); CA-exendin-4-PEG-Fc conjugate (HM1 1260C)+CA-glucagon; and CA-exendin-4-PEG-Fc conjugate (HM1 1260C)+CA-glucagon-PEG-Fc conjugate (LAPS CA-glucagon) at different doses for two weeks.

Here, for G2 group, the CA-exendin-4-PEG-Fc conjugate was administered at a dose of 20 μg/kg once a week; for G3 group, the CA-exendin-4-PEG-Fc conjugate, at a dose of 20 μg/kg once a week and the CA-glucagon, at a dose of 100 μg/kg twice a day (BID); for G4 group, the CA-exendin-4-PEG-Fc conjugate, at a dose of 20 μg/kg once a week and the CA-glucagon-PEG-Fc conjugate at a dose of 700 μg/kg once a week; and for G5 group, the CA-exendin-4-PEG-Fc conjugate, at a dose of 20 μg/kg once a week and the CA-glucagon-PEG-Fc conjugate, at a dose of 1400 μg/kg once a week.

Following the administration of each test material, mice in each group were monitored every day for changes in body weight, food intake and blood glucose level.

Figure 2:
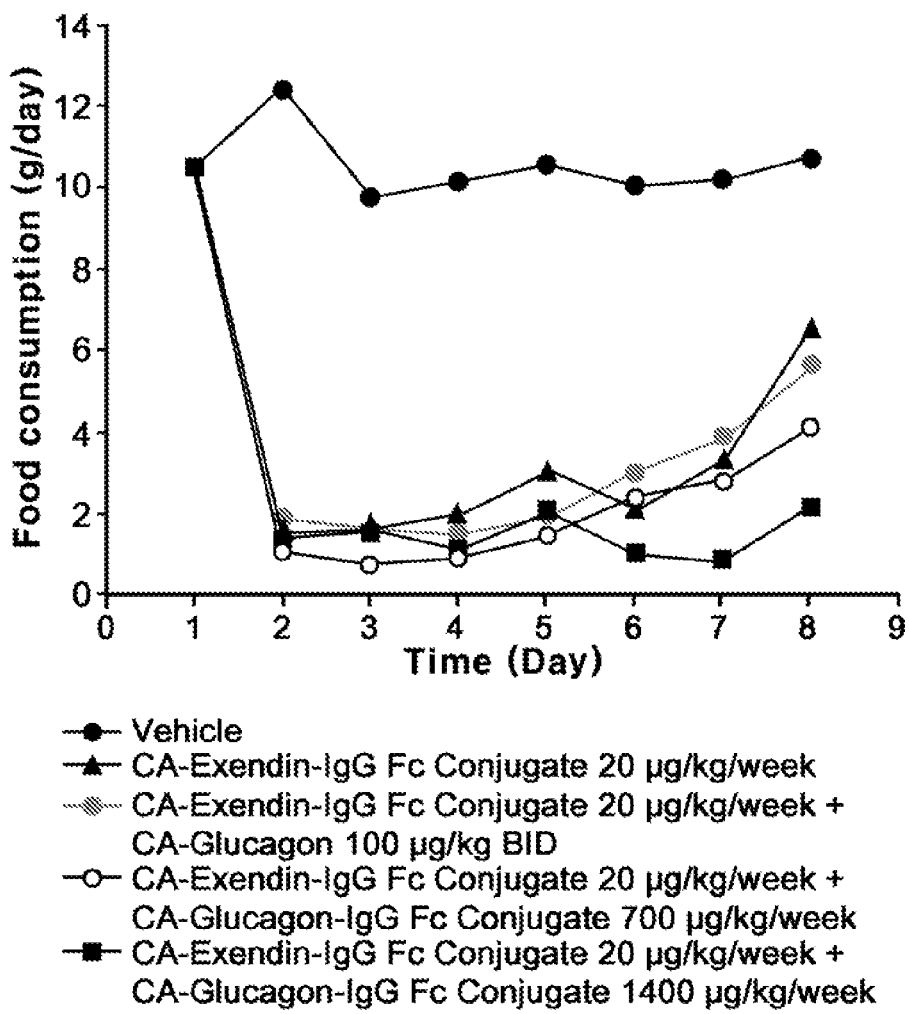
FIG. 2 is a graph showing changes in food intake of DIO (Diet-Induced Obesity) mice for 8 days after the co-administration of a long-acting CA-glucagon conjugate with a long-acting CA-exendin-4 conjugate.
Figure 3:
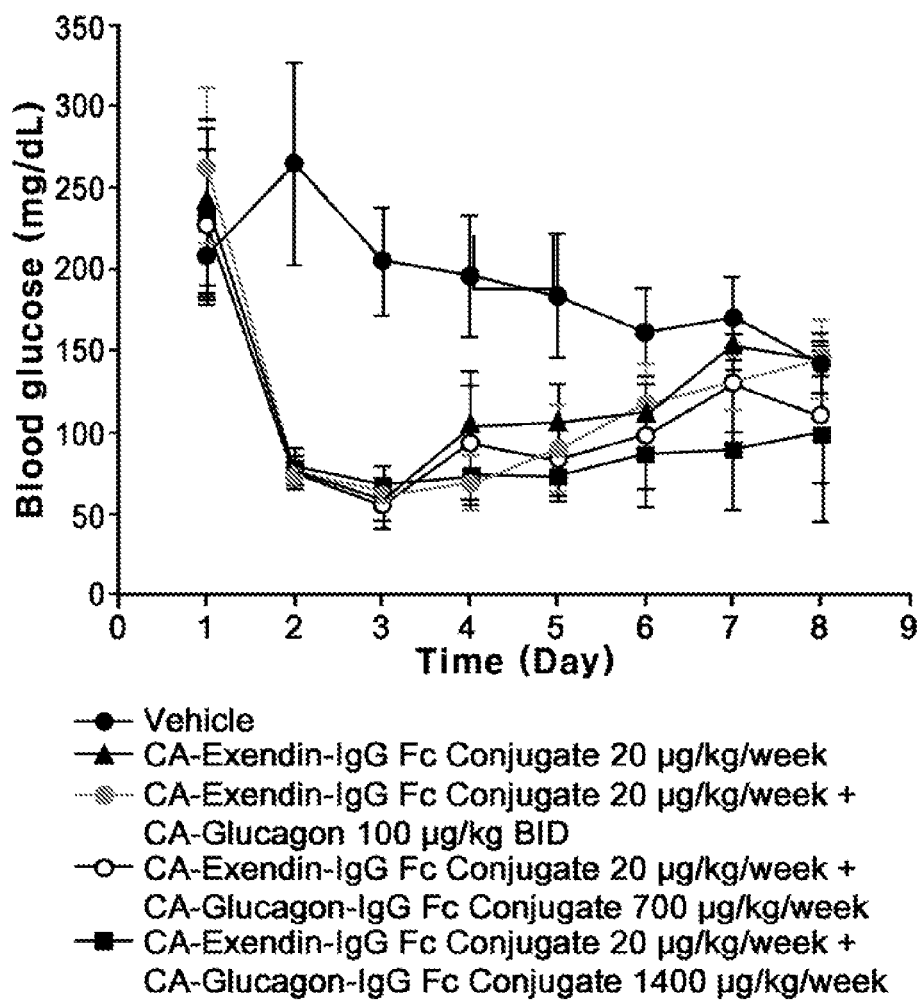
FIG. 3 is a graph showing changes in blood glucose level of DIO (Diet-Induced Obesity) mice for 8 days after the co-administration of a long-acting CA-glucagon conjugate with a long-acting CA-exendin-4 conjugate.
Figure 4:
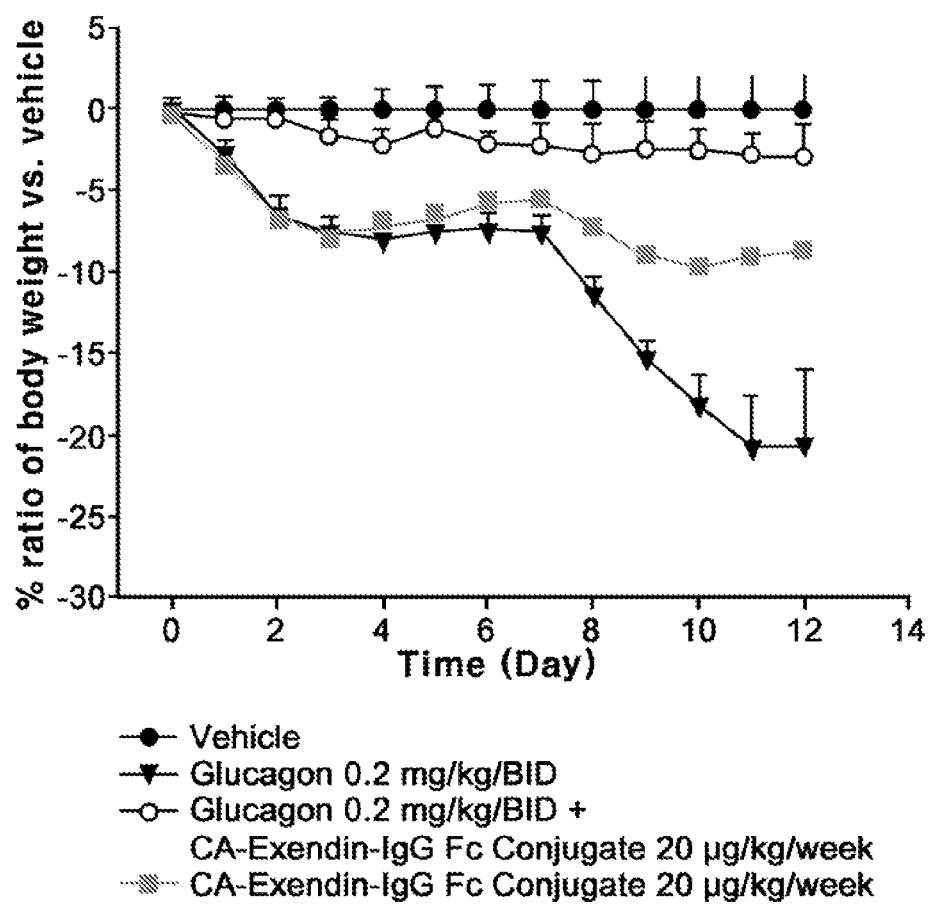
FIG. 4 is a graph showing changes in body weight of DIO (Diet-Induced Obesity) mice for 12 days after the co-administration of native glucagon with a long-acting CA-exendin-4 conjugate.
Figure 5:
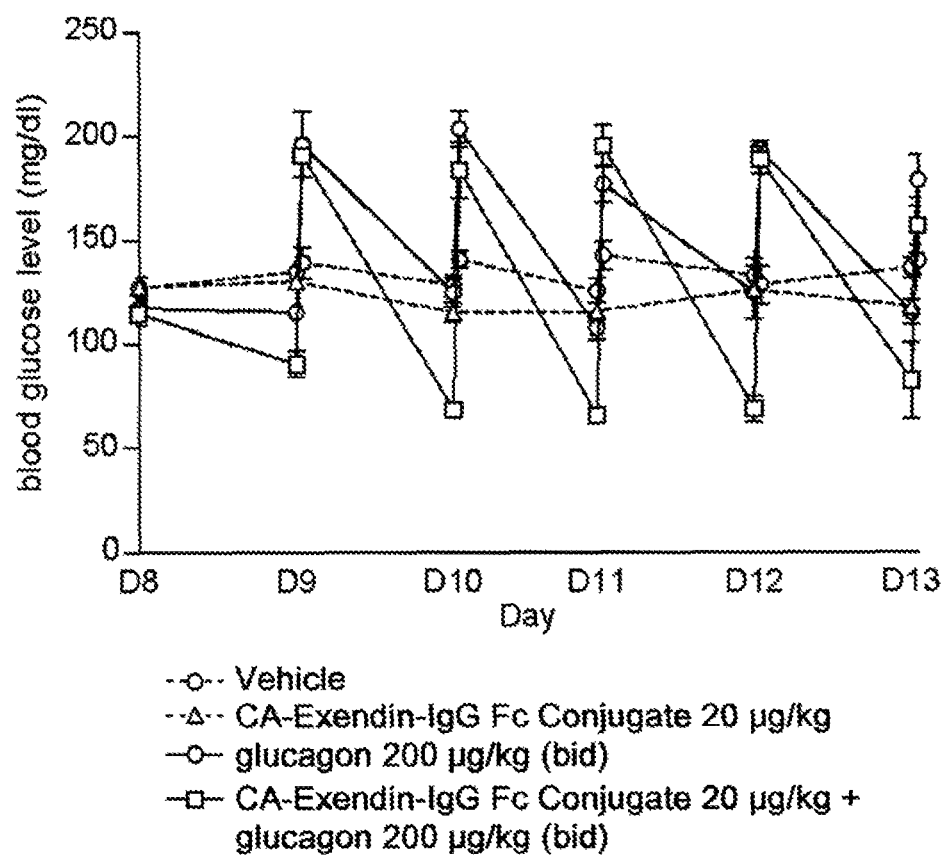
FIG. 5 is a graph showing changes in blood glucose level of DIO (Diet-Induced Obesity) mice for 12 days after the co-administration of native glucagon with a long-acting CA-exendin-4 conjugate.

As can be seen in FIGS. 1 to 3, the group co-administered with the long-acting glucagon conjugate and the long-acting exendin-4 conjugate showed a significant decrease in body weight and food intake, as compared with other groups. Particularly, the group co-administered with the native glucagon and the long-acting exendin-4 conjugate showed the loss of body weight, but severe fluctuation in blood glucose level was observed (FIGS. 4 and 5). However, the group co-administered with the long-acting glucagon conjugate and the long-acting exendin-4 conjugate exhibited stable fluctuation of blood glucose level.

These results suggest that only when both glucagon and exendin-4 being in the form of along-acting conjugate, the co-administration can induce a synergistic effect on the loss of bodyweight and suppression of food intake without fluctuation in blood glucose level. Further, it has been found that the long-acting conjugates of the present invention can be administered at a remarkably low dose due to its prolonged blood half-life and improved in-vivo durability, and thus can be effectively used for preventing or treating obesity.

Comparison Example 1

Co-Administration of Native Glucagon with an Anti-Obesity Drug

To confirm the effect upon the co-administration of native glucagon with the long-acting exendin-4 conjugate prepared in Example 2, diet-induced obesity (DIO) mice were administered respectively with a vehicle as a control (G1); native glucagon peptide (G2); CA-exendin-4-PEG-Fc conjugate (HM1 1260C)(G3); and native glucagon+CA-exendin-4-PEG-Fc conjugate (HM1 1260C)(G4) at different doses for two weeks, according to the same method as described in Example 3.

Here, for G2 group, the native glucagon was administered at a dose of 200 μg/kg twice a day (BID); for G3 group, the CA-exendin-4-PEG-Fc conjugate was administered at a dose of 20 μg/kg once a week; and for G4 group, native glucagon, at a dose of 200 μg/kg twice a day (BID) and the CA-exendin-4-PEG-Fc conjugate, at a dose of 20 μg/kg once a week.

Following the administration of each test material, mice in each group were monitored every day for changes in body weight, food intake and blood glucose level.

As can be seen in FIGS. 4 and 5, the group co-administered with the native glucagon and the long-acting exendin-4 conjugate showed the effect of body weight reduction higher than other groups, but severe fluctuation in blood glucose level was observed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The long-acting glucagon conjugate of the present invention shows a prolonged blood half-life and an improved in vivo durability and stability. Thus, when used in combination with an anti-obesity drug, the long-acting glucagon conjugate of the present invention can be administered at a remarkably low dose and exhibit an improvement in drug compliance without fluctuation in blood glucose level. Accordingly, the long-acting glucagon conjugate of the present invention can be effectively used for preventing or treating obesity.

The invention claimed is:

1. A long-acting glucagon conjugate in which a glucagon derivative is covalently linked to a polymer carrier via a non-peptide linker, wherein the glucagon derivative is selected from the group consisting of modified glucagons represented by the following Formulae 1 to 4:

<Formula 1>

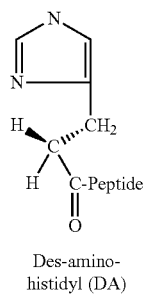

Des-amino-histidyl (DA)

<Formula 2>

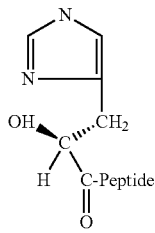

Beta-hydroxy-imidazopropionyl (HY)

<Formula 3>

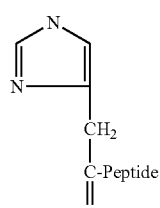

Imidazoacetyl (CA)

<Formula 4>

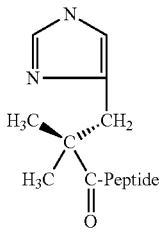

Dimethyl-histidyl (DM)

wherein "Peptide" represents native glucagon.

2. The long-acting glucagon conjugate of claim 1, wherein the non-peptide linker is covalently linked at one end thereof to the modified glucagon and at the other end thereof to a polymer carrier.

3. The long-acting glucagon conjugate of claim 1, wherein the non-peptide linker is selected from the group consisting of polyethylene glycol, polypropylene glycol, copolymers of ethylene glycol and propylene glycol, polyoxyethylated polyols, polyvinyl alcohol, polysaccharides, dextran, polyvinylethylether, biodegradable polymers, lipid polymers, chitin, hyaluronic acid and a combination thereof.

4. The long-acting glucagon conjugate of claim 1, wherein the non-peptide linker has a molecular weight ranging from 1 to 100 kDa.

5. The long-acting glucagon conjugate of claim 1, wherein the non-peptide linker has a functional group at both ends, the functional groups being the same or different.

6. The long-acting glucagon conjugate of claim 5, wherein the functional group is selected from the group consisting of aldehyde, propionaldehyde, butylaldehyde, maleimide, succinimidyl propionate, hydroxy succinimidyl carboxymethyl and succinimidyl carbonate.

7. The long-acting glucagon conjugate of claim 6, wherein the non-peptide linker has an aldehyde group at both ends.

8. The long-acting glucagon conjugate of claim 7, wherein the non-peptide linker is polyethylene glycol having an aldehyde group at both ends.

9. The long-acting glucagon conjugate of claim 1, wherein the polymer carrier is selected from the group consisting of polyethylene glycol, polyamino acids, albumin, gelatin, immunoglobulin fragments, dextran, fatty acids, polysaccharides and macromolecular polymers.

10. The long-acting glucagon conjugate of claim 9, wherein the polymer carrier is an immunoglobulin Fc fragment.

11. The long-acting glucagon conjugate of claim 10, wherein the immunoglobulin Fc fragment is aglycosylated.

12. The long-acting glucagon conjugate of claim 10, wherein the immunoglobulin Fc fragment is composed of one to four domains selected from the group consisting of $C_{H1}$, $C_{H2}$, $C_{H3}$ and $C_{H4}$ domains.

13. The long-acting glucagon conjugate of claim 10, wherein the immunoglobulin Fc fragment further comprises a hinge region.

14. The long-acting glucagon conjugate of claim 10, wherein the immunoglobulin Fc fragment is derived from an immunoglobulin selected from the group consisting of IgG, IgA, IgD, IgE and IgM.

15. The long-acting glucagon conjugate of claim 10, wherein the immunoglobulin Fc fragment is an IgG4 Fc fragment.

16. The long-acting glucagon conjugate of claim 15, wherein the immunoglobulin Fc fragment is an aglycosylated human IgG4 Fc fragment.

17. A long-acting glucagon conjugate in which a glucagon compound is covalently linked to a polymer carrier via a non-peptide linker, which has a structure represented by the following Formula 5:

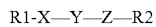      <Formula 5>

R1 is selected from the group consisting of histidine, des-amino-histidyl, N-dimethyl-histidyl, beta-hydroxy imidazopropyl and 4-imidazoacetyl;

R2 is selected from the group consisting of —$NH_2$, —OH and lysine;

X is SQGTFTSDYSKYLDSRRAQDFVQWLMNT (SEQ ID NO: 3);

Y is polyethylene glycol;

Z is an immunoglobulin Fc fragment.

18. A method for preparing the long-acting glucagon conjugate of claim 1, comprising the steps of:
1) reacting a non-peptide linker having a functional group at both ends with a glucagon derivative;
2) separating from the reaction mixture of step 1) a complex in which the glucagon derivative is covalently linked to one end of the non-peptide linker;
3) reacting the complex separated in step 2) with a polymer carrier; and
4) separating from the reaction mixture of step 3) a long-acting glucagon conjugate in which the non-peptide linker is covalently linked at one end thereof to the glucagon derivative and at the other end thereof to the polymer carrier, wherein the glucagon derivative is selected from the group consisting of modified glucagons represented by the following Formulae 1 to 4:

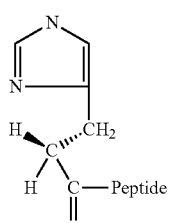

Des-amino-histidyl (DA)

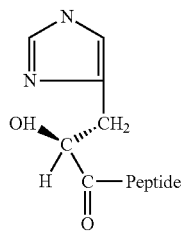

Beta-hydroxy-imidazopropionyl (HY)

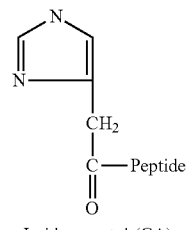

Imidazoacetyl (CA)

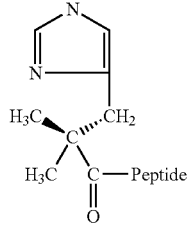

Dimethyl-histidyl (DM)

wherein "Peptide" represents native glucagon.

19. The method of claim 18, wherein the reaction between the glucagon or its derivative and the non-peptide linker in step 1) is performed at a molar ratio ranging from 1:5 to 1:50 at pH ranging from 7.5 to 10.0.

20. The method of claim 18, wherein the reaction between the glucagon derivative and the non-peptide linker in step 1) is performed in presence of a reducing agent.

21. The method of claim 20, wherein the reducing agent is selected from the group consisting of sodium cyanoborohydride, sodium borohydride, dimethylamine borate and pyridine borate.

22. The method of claim 18, wherein the complex separated in step 2) has a structure of glucagon-non-peptide linker in which the non-peptide linker is covalently linked at one end thereof to an amino acid residue other than the N-terminal end of the glucagon derivative.

23. The method of claim 22, wherein the amino acid residue is the 12th lysine residue of the glucagon derivative.

24. The method of claim 18, wherein the reaction between the complex and the polymer carrier in step 3) is performed at a molar ratio of from 1:2 to 1:10 at pH ranging from 5.0 to 8.0.

25. The method of claim 18, wherein the reaction between the complex and the polymer carrier in step 3) is performed in presence of a reducing agent.

26. The method of claim 25, wherein the reducing agent is selected from the group consisting of sodium cyanoborohydride, sodium borohydride, dimethylamine borate and pyridine borate.

27. The method of claim 18, wherein the long-acting glucagon conjugate separated in step 4) has a structure of glucagon-non-peptide linker-polymer carrier.

28. The method of claim 18, comprising:
1) reacting PEG having an aldehyde group at both ends with the glucagon derivative at pH 9.0;
2) separating from the reaction mixture of step 1) a glucagon derivative-PEG complex in which PEG is covalently linked at one end thereof to the 12th lysine residue of the glucagon derivative;
3) reacting the glucagon derivative-PEG complex separated in step 2) with an immunoglobulin Fc fragment; and
4) separating from the reaction mixture of step 3) a long-acting glucagon conjugate in which PEG is covalently linked at one end thereof to the glucagon derivative and at the other end thereof to the immunoglobulin Fc fragment.

29. A pharmaceutical composition, comprising the long-acting glucagon conjugate of claim 1 as an effective ingredient and a pharmaceutically acceptable carrier.

30. The pharmaceutical composition of claim 29, further comprising an anti-obesity drug.

31. The pharmaceutical composition of claim 30, wherein the anti-obesity drug is selected from the group consisting of GLP-1 agonists, leptin agonists, DPP-IV inhibitors, Y5 receptor antagonists, melanin-concentrating hormone antagonists, Y2/3 agonists, MC3/4 agonists, gastric/pancreatic lipase inhibitors, $5HT_{2c}$ agonists, βA agonists, amylin agonists, ghrelin antagonists and combinations thereof.

32. The pharmaceutical composition of claim 31, wherein the GLP-1 agonist is selected from the group consisting of exendin-4, an exendin-4 derivative and a long-acting conjugate thereof.

33. The pharmaceutical composition of claim 32, wherein the exendin-4 derivative is selected from the group consisting of a derivative in which an amine group of a first N-terminal histidine residue of native exendin-4 is deleted; a derivative in which an amine group of a first N-terminal histidine residue thereof is substituted with a hydroxyl group; a derivative in which an amine group of a first N-terminal histidine residue thereof is modified with two methyl groups; and a derivative in which an alpha-carbon of a first N-terminal histidine residue thereof and an amine group attached thereto are deleted.

34. The pharmaceutical composition of claim 32, wherein the long-acting exendin-4 conjugate has a structure in which exendin-4 or its derivative is covalently linked to an immunoglobulin Fc fragment via a non-peptide linker.

35. The pharmaceutical composition of claim 34, wherein the long-acting exendin-4 conjugate has a structure in which the non-peptide linker is covalently linked at one end thereof to an exendin-4 derivative and at the other end thereof to an immunoglobulin Fc fragment, said exendin-4 derivative being a derivative in which an alpha-carbon of a first N-terminal histidine residue thereof and an amine group attached thereto are deleted.

36. A method for treating obesity, comprising the step of administering the long-acting glucagon conjugate of claim 1 in a therapeutically effective amount to a subject in need thereof.

37. The method of claim 36, wherein the long-acting glucagon conjugate is administered in combination with an anti-obesity drug.

38. The method of claim 37, wherein the anti-obesity drug is selected from the group consisting of GLP-1 agonists, leptin agonists, DPP-IV inhibitors, Y5 receptor antagonists, melanin-concentrating hormone antagonists, Y2/3 agonists, MC3/4 agonists, gastric/pancreatic lipase inhibitors, $5HT_{2c}$ agonists, βA agonists, amylin agonists, ghrelin antagonists and combinations thereof.

39. The method of claim 38, wherein the GLP-1 agonist is selected from the group consisting of exendin-4, an exendin-4 derivative and a long-acting conjugate thereof.

40. The method of claim 39, wherein the exendin-4 derivative is selected from the group consisting of a modified exendin-4 in which an amine group of a first N-terminal histidine residue of native exendin-4 is deleted; a modified exendin-4 in which an amine group of a first N-terminal histidine residue thereof is substituted with a hydroxyl group; a modified exendin-4 in which an amine group of a first N-terminal histidine residue thereof is modified with two methyl groups; and a modified exendin-4 in which an alpha-carbon of a first N-terminal histidine residue thereof and an amine group attached thereto are deleted.

41. The method of claim 39, wherein the long-acting exendin-4 conjugate has a structure in which the exendin-4 or the exendin-4 derivative is covalently linked to an immunoglobulin Fc fragment via a non-peptide linker.

42. The method of claim 41, wherein the long-acting exendin-4 conjugate has a structure in which the non-peptide linker is covalently linked at one end thereof to the exendin-4 derivative and at the other end thereof to an immunoglobulin Fc fragment, said exendin-4 derivative being a modified exendin-4 in which an alpha-carbon of a first N-terminal histidine residue of native exendin-4 and an amine group attached thereto are deleted.

* * * * *